United States Patent [19]

Schick et al.

[11] Patent Number: 5,139,956
[45] Date of Patent: Aug. 18, 1992

[54] METHOD AND SYSTEM FOR DETERMINING PEROXIDE CONTENT

[75] Inventors: Karl G. Schick; Paul M. Karges, both of Milwaukee; Gary A. Lang, Brookfield; David A. Uhen, Palmyra, all of Wis.

[73] Assignee: FIAtron-Eppendorf, Inc., Madison, Wis.

[21] Appl. No.: 663,791

[22] Filed: Mar. 4, 1991

Related U.S. Application Data

[63] Continuation of Ser. No. 512,004, Apr. 12, 1990, abandoned, which is a continuation of Ser. No. 290,868, Dec. 27, 1988, abandoned, which is a continuation of Ser. No. 178,859, Apr. 8, 1988, abandoned, which is a continuation of Ser. No. 902,665, Sep. 2, 1986, abandoned.

[51] Int. Cl.$^5$ .................. G01N 21/01; G01N 21/75; G01N 31/22
[52] U.S. Cl. .................. 436/52; 422/62; 422/81; 422/82.05; 422/82.09; 436/135
[58] Field of Search ............ 422/62, 69, 81, 83, 422/88, 90, 98, 103, 82.05, 82.090; 436/135, 52; 73/836.72, 863.86

[56] References Cited

U.S. PATENT DOCUMENTS

| | | | |
|---|---|---|---|
| 3,222,133 | 12/1965 | Ballou et al. | 422/69 |
| 3,340,013 | 9/1967 | Rooney et al. | 422/90 |
| 3,427,135 | 2/1969 | Pelavin et al. | 422/82 |
| 3,787,197 | 1/1974 | Snyder et al. | 65/260 |
| 3,866,118 | 2/1975 | Ghosh et al. | 422/83 |
| 3,892,532 | 7/1975 | Bohlen | 422/69 |
| 4,035,149 | 7/1977 | Scott et al. | 422/42 |
| 4,106,905 | 8/1978 | Schmitt et al. | 422/42 |
| 4,142,859 | 3/1979 | Shaffer | 422/88 |
| 4,361,027 | 11/1982 | Schmitt | 422/88 |
| 4,402,910 | 9/1983 | Smith et al. | 422/83 |

Primary Examiner—Jill Johnston
Assistant Examiner—David Redding
Attorney, Agent, or Firm—Marshall, O'Toole, Gerstein, Murray & Bicknell

[57] ABSTRACT

The peroxide content of a non-aqueous medium is measured by a system including separate supplies for two carrier solutions, a first one containing an acid for acidifying the sample and the second containing an iodide compound for reacting with the peroxide(s) in the sample and producing a free iodine ion, such as $I_3^-$, and a flow-through detector, such as a colorimetric device. The sample and first carrier solution streams are controlled by a sample injection valve which is movable between a load position wherein the sample stream is routed to a sample waste collector via a sample loop and the first carrier solution stream passes through a first carrier solution conduit and is combined with a stream the second carrier solution prior to passing through the detector and a measure position wherein a slug of the sample is introduced into the first carrier solution conduit, mixed with the first carrier solution and combined with the second carrier solution prior to passing through the detector. The peroxide(s) in the sample reacts with the iodide compound in the second carrier solution to produce $I_3^-$ which is measured by the detector.

18 Claims, 1 Drawing Sheet

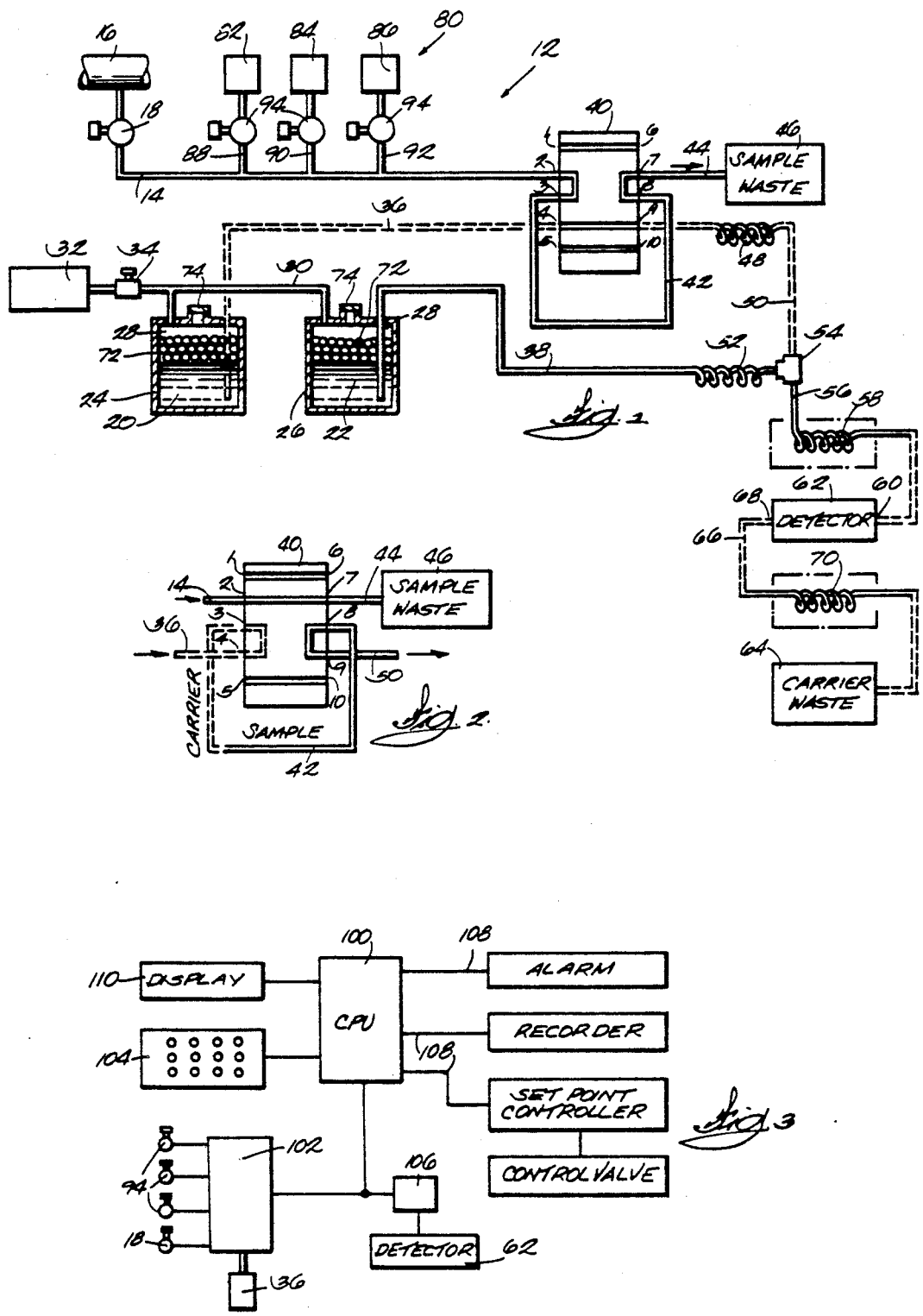

METHOD AND SYSTEM FOR DETERMINING PEROXIDE CONTENT

This application is a continuation of application Ser. No. 512,004, filed Apr. 12, 1990 now abandoned, which is a continuation of application Ser. No. 07/290,868 filed Dec. 27, 1988, now abandoned. Which is a continuation of application Ser. No. 07/178,859 filed Apr. 8, 1988, now abandoned which is a continuation of application Ser. NO. 06/902,665 filed Sep. 2, 1986, now abandoned.

BACKGROUND OF THE INVENTION

This invention relates to systems and methods for determining the peroxide or active oxygen content in non-aqueous liquid media.

Peroxides are used as initiators in a variety of chemical processes. The capability of making a rapid analysis of a feedstock or product stream for peroxide content is highly desirable. Adjustments can be made as required at frequent intervals to provide a desired concentration of peroxide for the process. Such close control of the peroxide content can result in reduced process costs because of higher yields and lower scrap and in improved quality control. Also, continuous monitoring of peroxide content is important for processes where peroxides decompose during processing and release oxygen which can reach explosive levels.

The technique most commonly used to determine peroxide content in a non-aqueous medium is a manual procedure (ASTM E299-68) involving a chemical reaction which is performed in the dark under a nitrogen blanket and takes approximately one hour to complete. In addition to being time consuming, this manual procedure requires relatively large amounts of reagents.

SUMMARY OF THE INVENTION

An object of the invention is to provide a simple system and method for rapidly analyzing a non-aqueous medium for peroxide content.

Another object of the invention is to provide such a system and method which can be used for on-line analysis of a process stream.

A further object of the invention is to provide such a system and method which can be fully automated.

A still further object of the invention is to provide such a system which employs pressurized reservoirs as the means for supplying continuous streams of carrier solutions and yet is not subject to significant outgassing or gas bubble formation.

A yet further object of the invention is to provide an automated system and method for analyzing the peroxide content of non-aqueous media including a colorimetric detector and the capability of introducing calibration solutions at programmable intervals and generating an updated calibration curve for the detector.

Other objects, aspects and advantages of the invention will become apparent to those skilled in the art upon reviewing the following detailed description, the drawing and the appended claims.

The invention provides a system and method capable of making an on-line analysis of a non-aqueous medium for peroxide content. The system includes means for supplying a continuous sample stream of a medium to be analyzed, means for supplying a continuous stream of a first carrier solution containing an acid, a flow-through detector, a sample loop or conduit means, a combined carrier solution conduit means connected in communication with the detector inlet, a first carrier solution conduit means connected in communication with the combined carrier solution conduit means, and means for supplying a continuous stream of a second carrier solution containing an iodide compound and including a second carrier solution conduit means connected in communication with the combined carrier solution conduit means. The sample and first carrier solution streams are controlled by a sample injection valve which is movable between a load position wherein the sample stream is routed to a sample waste collector via the sample loop and the first carrier solution stream passes through the first carrier solution conduit means and is combined with the second carrier solution stream prior to passing through the detector and a measure position wherein a slug of the sample is introduced into the first carrier solution conduit, mixed with the first carrier solution and then combined with the second carrier solution in the combined carrier solution conduit means prior to passing through the detector. The peroxide(s) in the sample reacts with the iodide compound in the second carrier solution to produce a free iodine ion, such as $I^-_3$, which is measured by the detector. The system also includes means for regulating liquid flow through the detector.

In one embodiment, a computer operates the sample injection valve between the load and measure positions at programmable intervals.

In one embodiment, liquid flow through the detector is regulated by a flow restrictor coil connected to the detector outlet and this coil is maintained at a predetermined, substantially constant temperature.

In one embodiment, the system is balanced so that the flow rates of the first and second carrier solutions are substantially equal prior to being combined. This can be accomplished by a flow balancing coil in each of the conduits through which the carrier solutions flow prior to being combined.

In one embodiment, intermixing of the sample and the carrier solutions is enhanced by a diffusion coil located between the sample injection valve and the detector. The diffusion coil can be heated to accelerate the reaction between the peroxide(s) and the iodide compound.

In one embodiment, separate supplies of calibration solutions containing known concentrations of $I_2$ are provided. A selector manifold, including a valve controlling sample flow and valves controlling flow of the calibration solutions, is operated at programmable intervals by the computer which generates an updated calibration curve for the detector.

In one embodiment, the carrier solutions are supplied from separate reservoirs pressurized with a substantially oxygen-free gas, such as helium. The carrier solution is isolated from the pressurizing gas by one or more layers of discrete, bubble-like objects floating on the surface of the carrier solution.

BRIEF DESCRIPTION OF THE DRAWINGS

FIG. 1 is a schematic diagram of the analyzing system of the invention shown with the sample injection valve in the load position.

FIG. 2 is a schematic diagram of the sample injection valve in the measure position.

FIG. 3 is a diagrammatic representation of an automatic control for the system.

DESCRIPTION OF THE PREFERRED EMBODIMENTS

While the system and method of invention can be used for a variety of applications, they are particularly adaptable for an on-line analysis for closed loop process control and will be described in connection with such an application.

Referring to FIG. 1, the analyzing system 12 includes a sample supply conduit 14 connected to a line 16 carrying the process stream to be analyzed. Pressure in the process delivers a continuous sample stream of a nonaqueous medium containing a peroxide(s) into the system through a two-way, pneumatically operated valve 18 in the supply conduit 14.

First and second carrier solutions 20 and 22 are contained in respective reservoirs 24 and 26. The first carrier solution 20 includes an organic solvent in which the sample and other reagents used in the system are miscible and an acid for creating an acidic environment for the reaction described below. The second carrier solution 22 includes an iodide compound capable of reacting with peroxide(s) in the sample to produce a free iodine ion, such as $I^-_3$, and an organic solvent in which the sample, iodide compound and other reagents used in the system are soluble.

Both carrier solutions 20 and 22 are pressurized with a substantially oxygen-free gas 28, such as helium, supplied to reservoirs 24 and 26 through a conduit 30 from a suitable source 32 and regulated to a desired pressure by a regulator 34 in the conduit 30. The pressurized reservoirs 24 and 26 deliver continuous streams of the first and second carrier solutions through respective supply conduits 36 and 38.

The sample supply conduit 14 and the first carrier solution supply conduit 36 are connected to a sample injection valve, which in the preferred embodiment illustrated is a conventional, pneumatically-operated, slider type valve 40 (e.g., CP Valve marketed by Bendix Corp.). Other suitable type valves, such as a rotary valve, can be used.

When the slider valve 40 is in the load position illustrated in FIG. 1, the sample stream enters the valve 40 through port 2, exits the valve 40 through port 3, passes through an external sample conduit or loop 42, reenters the valve 40 through port 8, exits again through port 7 and passes through a sample waste conduit 44 into a sample waste receptacle 46. At the same time, the first carrier solution stream enters the valve 40 through port 4, exits the valve 40 through port 9, passes through a flow balancing coil 48 including a length of coiled tube connected in a first carrier solution conduit 50. Also at the same time, the second carrier solution stream passes through a flow balancing coil 52 including a length of coiled tubing connected in the second carrier solution supply conduit 38.

The first carrier solution conduit 50 and the second carrier solution supply conduit 38 are connected together via a T-connector 54 which is connected to a combined carrier solution conduit 56. The first and second carrier solutions are mixed together as they pass through a diffusion coil 58 including a length of coiled tubing wrapped with a thermostatically controlled heating blanket (not shown) and connected in the combined carrier solution conduit 56. This heating blanket maintains the diffusion coil 58 at a substantially constant temperature (e.g., about 70° C.).

The combined carrier solution conduit 58 is connected to the inlet 60 of a flow through detector 62 capable of measuring the oxidation potential of the liquid flowing therethrough. In the preferred embodiment illustrated, the detector is a conventional dual beam, flow-through type colorimetric detector capable of producing an electrical signal representative of $I^-_3$ content of a liquid flowing therethrough (e.g., FIA-LITE 600 marketed by Fiatron Systems, Inc.). Other type detectors capable of measuring $I_2$ ions, such as by ultraviolet techniques, or $I^-_2$ ions, such as by an ion selective electrode, can be used.

The liquid stream passing through the detector 62 is routed to a carrier waste receptacle 64 by a carrier waste conduit 66 connected to the outlet 68 of the detector 62. The flow rate of this liquid stream is controlled by a flow restrictor coil 70 including a length of coiled tubing wrapped with a thermostatically controlled, electric heating blanket (not shown). This heating blanket maintains the flow restrictor coil 70 at a substantially constant temperature (e.g., about 70° C.).

When the slider valve 40 is moved to the measure position illustrated in FIG. 2, the sample stream enters the valve 40 through port 2, exits the valve 40 through port 7 and passes directly to the sample waste receptacle 46. At the same time, the first carrier solution 20 enters the valve 40 through port 4, exits the valve 40 through port 3, passes through the sample loop 42, reenters the valve 40 through port 8 and exits again through port 9. Thus, a slug of the sample having a volume corresponding to the internal volume of the sample loop 42 (e.g., 55 microliters) is introduced into the carrier solution conduit 50. As this sample slug and the first carrier solution passes through the carrier solution conduit 50, they are at least partially mixed together and the sample becomes acidified.

When this acidified mixture is mixed with the second carrier solution 22 in the combined carrier solution conduit 56 in the preferred embodiment, the peroxide(s) react with the iodide compound to produce free $I_3$. This is a two-step reaction which can be represented as follows:

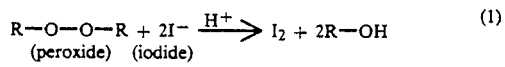

(1)

(2)

As mentioned above, the acid in the first carrier solution 20 provides the acidic environment required for reaction (1). Typically, acetic acid (80 g/1) is used; however, other organic acids having a pKa within the range of about 4 to about 5 can be used. Other suitable acids include benzoic acid (pKa=4.18), citric acid (pKa=4.74), oxalic acid (pKa=4.21) and tartaric acid (pKa=4.74), with acetic acid being preferred. pKa is a representation of alkalinity or acid of the solvent in an aqueous medium.

The organic solvent for the first carrier solution is miscible with the sample and substantially all of its components, the acid, and the iodide compound in the second carrier solution. The organic solvent should not absorb light in the wave length of $I^-_3$ (520 nm). It should have a relatively high boiling point so it does not volatize when heated during the passage through the diffusion coil 58 and the flow restrictor coil 70 and a relatively low freezing point so it does not solidify at lower ambient temperatures in colder climates. Suitable organic solvents include isopropyl alcohol, n-butanol and other alcohols, polyols and chlorinated hydrocarbons containing 3 to 8 carbon atoms, with isopropyl alcohol being preferred.

The concentration of acid in the first carrier solution is sufficient to acidify and buffer the sample. As a guide, this acid concentration can be on the order of 80 ml/1.

The system and method can be used to analyze for peroxides of varying reactivity such as hydroperoxides, diacyl peroxides, diaroyl peroxides, peresters and ketone peroxides which react with the iodide compound in the second carrier solution under normal system operating conditions.

The iodide compound used in the second carrier solution is capable of reacting with the peroxide(s) in the sample and producing free $I_3$. Suitable iodide compounds include sodium iodide and potassium iodide, with sodium iodide being preferred.

The organic solvent for the second carrier solution preferably is the same as that used in the first carrier solution. The second carrier solution contains an amount of the iodide compound at least sufficient to produce a one mole of $I^-_3$ for each mole of peroxide present in the sample. As a guide, for a system adapted to analyze concentrations of peroxides up to about 1.0 weight %, the concentration of sodium iodide in the second carrier solution can be on the order of about 50 g/1.

The diffusion coil 58 provides radial mixing and thereby enhances intermixing of the sample and the carrier solutions prior to flow through the detector 62. The diffusion coil 58 also can be used to heat the reaction medium to accelerate the above reactions. This temperature depends on the reactivity of the particular peroxide or peroxides present in the sample. If a relatively stable peroxide such as t-butyl hydroperoxide is present, a substantial amount of heat is required to accelerate the reaction and the diffusion coil 58 is maintained at a temperature of about 70° C. On the other hand, if a more reactive peroxide such as hydrogen peroxide is present, the reaction is exothermic and it may not be necessary for the diffusion coil 58 to be heated.

The flow rates of the first and second carrier solution streams are balanced by the flow balancing coils 48 and 52. These coils are dimensioned to provide the same flow rates through the first carrier solution conduit 50 and the second carrier solution supply conduit 38. The overall flow rate through the detector 62 is controlled by the flow restrictor coil 70. Thus, when the system is to have an overall flow rate of about 1.5 to 2.0 ml/min, the flow balancing coils 48 and 52 are dimensioned to provide a flow rate for each carrier solution stream greater than about 0.75 to 1.0 ml/min and the flow resistor coil 50 is dimensioned to provide the desired overall flow rate through the detector 62.

The use of relatively long, coiled tubing (e.g., 7 meters) to provide the pressure drop required to obtain the desired overall flow rate permits the use of a cross sectional flow area (e.g., 0.02" inside diameter) which is large enough to prevent plugging by particulate matter in the sample. A single plate orifice small enough to provide the required pressure drop is subject to becoming plugged by such particulate matter. Maintaining the flow restrictor coil 70 at a substantially constant temperature minimizes variations in flow through the detector 62 due to changes in ambient temperature.

The presence of gas bubbles in the system can adversely affect the accuracy of the measurements made by the detector 62. The carrier solution reservoirs usually are pressurized to about 25 psig and, if fully exposed to the pressurizing gas, the carrier solutions could absorb a considerable amount of the gas within a few hours. Helium is the preferred pressurizing gas because, in addition to being oxygen-free, it is relatively insoluble in many organic solvents.

To further minimize potential outgassing by gas absorbed in the carrier solutions, both carrier solution reservoirs 24 and 26 are provided with means for substantially isolating the pressuring gas from the carrier solution or, stated in another way, for minimizing the effective surface area of the carrier solution exposed to the pressurizing gas. In the preferred embodiment illustrated, discrete bubble-like objects or hollow spheres 72 are floated on the surface of the carrier solution for this purpose. The spheres 72 are made from material which is substantially inert with respect to the carrier solution. Two or more layers of the spheres 72 provide better isolation and, therefore, are preferred. As a guide, it has been found that three layers of $\frac{3}{4}$-inch, hollow polypropylene spheres about $1\frac{1}{2}$ to 2 inches deep provide satisfactory protection against significant absorption of helium by the carrier solutions.

A quick-disconnect type filler connection 74 can be provided on the reservoirs 24 and 26 so that carrier solution can be added to the reservoirs without introducing significant amounts of air.

The calibration of the detector 62 tends to change because of changes in ambient temperature, normal instrumentation drift, etc. The system includes means for introducing a plurality of calibration solutions (e.g., up to three) at programmable intervals and generating an updated calibration curve for the detector 62.

The illustrated preferred embodiment includes a selector manifold 80 including the sample valve 18 and three separate calibration solution reservoirs 82, 84 and 86 pressurized to about 5 psi and connected to the sample conduit 14 via respective calibration conduits 88, 90 and 92. Each calibration conduit includes a two-way, pneumatically-operated valve 94 which is selectively opened to introduce the corresponding calibration solution into the sample conduit 14. Each calibration solution contains a known concentration of $I_2$ dissolved in an organic solvent, preferably the same as the one used in the first and second carrier solutions. $I_2$ is used as a surrogate standard because most peroxides are too unstable to be used as standards. As a guide, $I_2$ concentrations for the three different calibration solutions can be 200, 500 and 1,000 mg/1.

When the system is in the calibrating mode, the sample valve 18 is closed and one valve 94 is opened with the slider valve 40 in the load position. After the sample loop 42 is filled with a first calibration solution, the slider valve 40 is moved to the measure position and a slug of the calibration solution is first mixed with and acidified by the first carrier solution. It thereafter reacts with the iodide compound in the second carrier solution, as illustrated in reaction (2) above to, produce free $I^-_3$. The detector 62 measures the $I^-_3$ content as described above and produces an output signal corresponding to the $I_2$ content of the calibration solution. The slider valve 40 is returned to the load position, another valve 94 is opened to fill the sample loop with a second calibration solution and the above cycle repeated for the second and third calibration solutions.

After the last calibration has been completed, the sample valve 18 is reopened. The sample waste conduit 44 preferably has no flow restrictions so that the sample supply conduit 14, the sample loop 42 and the slider valve 40 can be rapidly flushed out before, between and after calibrations.

Since $I_2$ is highly corrosive, all tubing contacted by the calibration solution preferably is made from a corrosion resistant material such as Teflon, the valves 94 preferably are lined with such a material, and the slider valve 40 is made from a corrosion-resistant material such as stainless steel or the like.

FIG. 3 is a diagrammatic representation of an automatic control for the system. Operation of the slider valve 40, the sample valve 18 and the calibration solution valves 94 is controlled by the central processing unit (CPU) 100 of a microprocessor (e.g. Z80 microprocessor marketed by Zylog) which transmits signals to a valve driver board 102 connected to those valves. The valve driver 102, through on-off switches, controls the pilot valves which pneumatically operate the slider valve 40, the sample valve 18 and the calibration valves 94. The CPU 100 includes a real time computer program which initiates electrical signals for moving the slider valve 40 between the load and measure positions and for opening and closing the sample valve 18 and the calibration solution valves 94. The time intervals for making an analysis and calibrations are programmable and can be changed by inputting the appropriate data with a key pad 104 connected to the CPU 100.

The output signal of the detector 62 is sent to a signal processing and analog/digital converter (A/D) board 106. The A/D board 106 converts the analog signals from the detector 62 to digitized signals which are transmitted to the CPU 100.

The CPU 100 contains a computer program which reads the signals from the A/D board 106 and initiates electrical signals (represented by lines 108) which, for example, can be used to trigger an alarm, drive a recorder and/or serve as an input to an automated process control system including a set point controller which operates a control valve. A vacuum flourescent display 110 provides a visual readout of the current operating conditions or program parameters. The CPU 100 also includes a computer program which reads the signals from the A/D board 106 during the calibration mode and stores an updated calibration curve for the detector 62. This calibration curve becomes the standard to which signals from the detector 62 during the measure mode are compared to produce the output signals 108.

From the foregoing description, one skilled in the art can easily ascertain the essential characteristics of the invention, and without departing from the spirit and scope thereof, make various changes and modifications to adapt it to various usages.

We claim:

1. An automated apparatus for determining the peroxide content of a non-aqueous liquid sample comprising:
   i) means for supplying a continuous stream of the non-aqueous liquid sample to a sample supply conduit;
   ii) means for supplying a continuous stream of a first carrier solution containing an acid reagent to a first carrier solution supply conduit comprising a first reservoir containing the first carrier solution, means for pressurizing the first carrier solution in the first reservoir to a predetermined pressure with a substantially oxygen-free gas, and means for substantially isolating the pressurizing gas from the first carrier solution wherein the first carrier solution supply conduit is connected in linear relationship with the first reservoir and a sample injection valve;
   iii) a sample injection valve connected to the sample supply conduit and the first carrier solution supply conduit wherein the sample injection valve is positionable between aload position having the first carrier solution supply conduit connected to a first carrier solution conduit and a sample collection conduit connected between the sample supply conduit and a sample waste collecting means wherein the sample collection conduit has two ends with both ends being connected to the sample injection valve, and
   a measure position having the sample supply conduit connected to the sample waste collecting means and the sample collection conduit connected between the first carrier solution supply conduit and the first carrier solution conduit which initially combines the sample with the first carrier solution and then combines with a second carrier solution in a combined carrier solution conduit before flowing through a detector means,
   iv) sample waste collection means connected in linear relationship with the sample supply conduit and connected to the sample injection valve,
   v) means for supplying a continuous stream of a second carrier solution to a second carrier solution supply conduit comprising a second reservoir containing the second carrier solution which comprises an iodide reagent, means for pressurizing the second carrier solution in the second reservoir to a predetermined pressure with a substantially oxygen-free gas, and means for substantially isolating the pressurizing gas from the second carrier solution wherein the second carrier solution supply conduit is connected in linear relationship with the second reservoir and the combined carrier solution conduit;
   vi) said detector means for producing a signal of the peroxide content of said non-aqueous liquid sample by detecting a reaction of the peroxide with the iodine reagent wherein the detector has an inlet connected to the combined carrier solution conduit and an outlet connected to a means for regulating liquid flow through said detector means.

2. An apparatus according to claim 1 including a diffusion coil constructed so as to mix the sample and the first and second carrier solutions, said coil including a length of coiled tubing connected to the combined carrier solution conduit upstream of the detector inlet.

3. An apparatus according to claim 2 including means for heating the diffusion coil to a predetermined temperature.

4. An apparatus according to claim 1 including means for regulating flow through the fist and second carrier solution supply conduits so that the flow rates through both the fist and second carrier solution supply conduits are substantially equal.

5. An apparatus according to claim 4 wherein the flow regulating means includes
   a first flow balancing coil including a length of coiled tubing connected to the fist carrier solution conduit between the sample injection valve and the diffusion coil; and a second flow balancing coil including a length of coiled tubing connected to the second carrier solution supply conduit upstream of the diffusion coil.

6. An apparatus according to claim 5 including means for heating the first and second balancing coils to a predetermined temperature.

7. An apparatus according to claim 1 wherein the sample supply means comprises:
a sample supply valve constructed and arranged so as to selectively connect the sample supply conduit with a source of the sample;
at least one source of a calibration solution containing a known concentration of $I_2$;
a calibration valve constructed and arranged so as to selectively admit the calibration solution into the sample supply conduit; and
means for selectively opening and closing the sample supply valve and the calibration valve at a programmable interval to generate an updated calibration curve of the detector means as the calibration solution flows therethrough.

8. An apparatus according to claim 1 wherein the combined carrier solution flowing through the detector means contains free $I_3$ and the detector means is a colorimetric device.

9. An apparatus according to claim 1 wherein the flow through the detector means is regulated by a flow restrictor coil connected to the detector outlet.

10. An apparatus according to claim 9 including means for heating the flow restrictor coil connected to the deectyor means outlet to a predetermined temperature.

11. A method for determining the peroxide content of a non-aqueous liquid sample comprising the steps of:
a) supplying a continuous stream of the non-aqueous liquid sample to a conduit connected to a detector;
b) supplying a continuous stream of a first carrier solution containing an acid reagent by pressurizing a first reservoir containing the first carrier solution to a predetermined pressure with a substantially oxygen-free gas that is substantially isolated from the first carrier solution to the conduit; p1 c) supplying a continuous stream of a second carrier solution containing an iodide compound by pressurizing a second reservoir containing the second carrier solution to a predetermined pressure with a substantially oxygen-free gas that is substantially isolated from the second carrier solution to the conduit;

(d) mixing a continuous stream of the first carrier solution with a predetermined volume of the sample in the conduit to give a first solution;
(e) mixing the first solution with a continuous stream of the second carrier solution in the conduit to react the iodide compound therein with peroxide in the sample to produce iodine ions in a first combined solution;
(f) passing the first combined solution through the detector;
(g) producing a signal representative of the concentration of the iodine ion in the first combined solution and calculating the concentration of peroxide based on the concentration of the iodine ion;
(h) repeating steps (b)–(g) each time an analysis is desired.

12. A method according to claim 11 wherein the iodine ion produced in step (c) is $I_3$ and the detector is a colorimetric device.

13. A method according to claim 11 including the step of regulating the liquid flow through the detector with a flow restrictor coil connected to the detector outlet.

14. A method according to claim 11 including the step of balancing the flows of the first and second carrier solutions so that the flow rates thereof are substantially equal before being the mixing of step (e).

15. A method according to claim 11 including the step of heating the first combined solution to a predetermined temperature before to passing through the detector.

16. A method according to claim 11 including the steps of:
(i) mixing at least one calibration solution containing a known concentration of $I_2$ with the first carrier solution and then with the second carrier solution to give a second combined solution;
(j) passing the second combined solution through a detector;
(k) producing a signal representative of $I_2$ content of the second combined solution, and
(l) repeating step (i) and (k) to obtain a signal for an updated calibration curve for the detector.

17. A method according to claim 11 including the step of floating one or more layers of a discrete, substantially inert bubble-like material on the surface of each carrier solution to minimize the absorption of the gas into the first and second carrier solutions.

18. A method according to claim 11 wherein the first carrier solution comprises acetic acid and isopropyl alcohol and the second carrier solution comprises sodium iodide and isopropyl alcohol.

* * * * *